US006562359B2

(12) United States Patent
Watanabe et al.

(10) Patent No.: US 6,562,359 B2
(45) Date of Patent: May 13, 2003

(54) PEST REPELLENT

(75) Inventors: Keisuke Watanabe, Ashiya (JP); Takao Ishiwatari, Toyonaka (JP)

(73) Assignee: Sumitomo Chemical Company, Ltd., Osaka (JP)

( * ) Notice: Subject to any disclaimer, the term of this patent is extended or adjusted under 35 U.S.C. 154(b) by 0 days.

(21) Appl. No.: 09/106,847

(22) Filed: Jun. 30, 1998

(65) Prior Publication Data

US 2002/0006424 A1 Jan. 17, 2002

(30) Foreign Application Priority Data

Jun. 30, 1997 (JP) .............................................. 9-173738
Jan. 8, 1998 (JP) ........................................... 10-002241

(51) Int. Cl.$^7$ .............................................. A01N 25/34
(52) U.S. Cl. ....................... 424/403; 424/406; 424/411; 424/750; 514/919
(58) Field of Search ................................ 424/403, 406, 424/DIG. 10, 750, 411; 514/919

(56) References Cited

U.S. PATENT DOCUMENTS 5,227,163 A * 7/1993 Eini et al. ................. 424/195.1
5,246,693 A * 9/1993 Grollier et al. ................ 424/70
5,518,736 A * 5/1996 Magdassi .................... 424/451

OTHER PUBLICATIONS

Merck Pinene p 835 Oil of Hyssop p. 759, 1968.*
Hoffmann Hyssop p. 104, 1996.*
Culpeper The Complete Method p. 134–135 Hyssop 1995.*
Chen: CN 1044205 Dec. 1989.*
Hcaplur Abstract DN 116:17209.*
Novak—Translation Biologia (Bratislava) No. 29, vol. 5 pp. 445–447, 1974.*
Merck Manual p. 1840, 1972.*
DReirbach Handbook of Poisoning p. 160, 1971.*
D. Novak, "Note On The Use of Some Plants, Plant Extracts and Oils in Insect Control," Biologia, Czechoslovakia, (1974) vol. 29, No. 5, pp. 445–447.
J. W. Dover, "The Responses of Some Lepidoptera To Labiate Herb and White Clover Extracts," Biological Abstracts, vol. 81, Philadelphia, PA, US, Abstract No. 51547.
F. Mansour et al., "Studies of the Effects of Essential Oils Isolated from 14 Species of Labiatae on the Carmine Spider Mite Tetranychus–Cinnabarinus," Biological Abstracts, vol. 83, Philadelphia, PA, US, Abstract No. 12580.

* cited by examiner

Primary Examiner—Neil S. Levy
(74) Attorney, Agent, or Firm—Fitch, Even, Tabin & Flannery

(57) ABSTRACT

This invention provides a pest repellent of the type which is not only applied to the skin directly but capable of preventing harm from the noxious insects, especially bloodsuckers such as mosquitoes and flies, by inhibiting them from entering the inside of the dwelling. The pest repellent is characterized in that it contains hyssop oil as an active ingredient.

6 Claims, No Drawings

PEST REPELLENT

The present invention relates to a pest repellent.

Hitherto, in order to protect the bodies of human and animals from bloodsucking insects such as mosquitoes and flies, pest repellents such as N,N-diethyl-m-toluamide (hereinafter referred to as "DEET") have been used by directly applying them to the skin of human and animals. However, a satisfactory pest repelling effect of DEET has not been obtained by spraying the compound in the inside of a house or supporting the compound on a suitable carrier and placing it in the inside of a house, aside from the case of direct application to the skin.

The object of the present invention is to provide a pest repellent which can be used effectively not only in direct application to the skin but also in various other ways of use including spraying in the inside of a house or on furniture.

As a result of studies conducted for finding out a pest repellent which can answer the above object, the present inventors found that hyssop oil is useful as an active ingredient of said pest repellents and attained the present invention.

Thus, the present invention relates to a pest repellent using hyssop oil as active ingredient, and a pest repelling method using hyssop oil. A pest can be effectively repelled according to the present method.

The hyssop oil used in the present invention is an essential oil of a plant hyssop (*Hyssopus officinalis* L.) which can be obtained from steam distillation of green or dry grass of hyssop. Hyssop oil is also commercially available from, for instance, Takasago Koryo KK and Hasegawa Koryo KK, and the commercially available hyssop oil can be used as they are.

The pests against which the pest repellent of the present invention is effective include noxious invertebrates, for example, anthropods such as insects, arachnids, crustaceans, chilopods and diplopods, and mollusks such as snails and slugs. Examples of the insects include the noxious insects of the order Diptera, for example, anopheles, aedes such as *Aedes aegypti* and *Aedes albopictus,* culexes such as *Culex pipiens* and *Culex tritaeniorhynchus,* gnat, stable fly, sand fly, biting midge, house fly, vinegar flies and moth flies; the order Dictyoptera such as German cockroach, smokybrown cockroarch, American cockroach, brown cockroach and oriental cockroach; the order Coleoptera such as rice weevil, adzuki bean weevil, red flour beetle, black carpet beetle, varies carpet beetle, powder post beetle, and *Paederus fuscipes;* the order Hymenoptera such as ants, wingless wasps and bethylid wasps; the order Siphonaptera such as Pulex; the order Anoplura such as *Pediculus humanus* and *Phthirus pubis;* and the order Isoptera such as *Reticulitermes speratus* and *Coptotermes formosanus.* Examples of the arachnids include house dust mites such as common grain mites, *Dermatophagoides farinae* and Cheyletid mites, *Ornithonysus bacoti,* Ixodides such as *Boophilus microplus* and spiders. Examples of the crustacea include Oniscoidea such as sow bug and wood louse. Examples of the chilopods include centipede and millipede. Examples of the diplopods include wireworm. The pest repellent of the present invention can also be applied to the plants to inhibit sap-sucking behavior of aphids, thereby to prevent propagation of plant disease infectious virus hosted by such pests. Therefore, the pest repellent of the present invention can be used for the purpose of protecting plants.

In the present invention, hyssop oil may be used directly for repelling of pests, but usually a carrier is added to hyssop oil to form a liquid formulation (such as aerosol), cream or the like, or hyssop oil is impregnated in a synthetic resin for forming a resin molding. Also, hyssop oil may be impregnated in a paper, cloth or unglazed pottery, or may be formulated into a gel-type formulation, and then used.

As the carrier employed in forming liquid formulations, there can be used, for example, water; alcohols such as methanol, ethanol, glycerin and polyethylene glycol; ethers such as tetrahydrofuran and dioxane; aliphatic hydrocarbons such as hexane, kerosine, paraffin and petroleum benzine; and esters such as ethyl acetate.

In the liquid formulations, it is possible to blend commonly used adjuvants or auxiliary agents such as emulsifying or dispersing agent, spreading agent, wetting agent, suspending agent, preservative, propellant and film-forming agent. Examples of the emulsifying or dispersing agents usable in the present invention include soaps, polyoxyethylene fatty acid alcohol ethers such as polyoxyethylene oleyl ether, polyoxyethylene alkylaryl ethers such as polyoxyethylene nonylphenyl ether, polyoxyethylene fatty acid esters, fatty acid glyceride, sorbitan fatty acid esters, sulfuric esters of higher alcohols, and alkylaryl sulfonates such as sodium dodecylbenzenesulfonate; examples of the spreading and wetting agents include glycerin and polyethylene glycol; examples of the suspending agents include casein, gelatin, alginic acid, carboxymethyl cellulose, gum arabic, hydroxypropyl cellulose and bentonite; examples of the preservatives include methyl p-hydroxybenzoate, ethyl p-hydroxybenzoate, propyl p-hydroxybenzoate, and butyl p-hydroxybenzoate; examples of the propellants include dimethyl ether, chlorofluorocarbons and carbon dioxide; and examples of the film forming agents include nitrocellulose, acetyl cellulose, acetylbutyl cellulose, methyl cellulose derivatives, vinyl resins such as vinyl acetate resin, and polyvinyl alcohol.

The carriers usable in the preparation of cream formulations include hydrocarbons such as liquid paraffin, vaseline and paraffin; silicones such as dimethylsiloxane, colloidal silica and bentonite; monohydric alcohols such as ethanol, stearyl alcohol, lauryl alcohol and cetyl alcohol; polyhydric alcohols such as polyethylene glycol, ethylene glycol and glycerin; carboxylic acids such as lauric acid and stearic acid; and esters such as beeswax and lanoline. In the cream formulations, there may also be blended the adjuvants or auxiliary agents same as used in said liquid formulations.

The synthetic resins usable for forming the resin moldings include polyethylene; polypropylene; copolymers of ethylene and monomers having polar groups, such as ethylene-vinyl acetate copolymer, ethylene-methyl acrylate (or methacrylate) copolymer, ethylene-ethyl acrylate copolymer, and ethylene-vinyl acetate-methyl acrylate (or methacrylate) copolymer; and chlorine-containing synthetic resins such as polyvinyl chloride and polyvinylidene chloride. Of these substances, ethylene-vinyl acetate copolymer or ethylene-methyl methacrylate copolymer is preferred in view of thermoforming properties (low-temperature processability), and hyssop oil absorbing properties, diffusibility and stability.

Impregnation of hyssop oil into synthetic resin can be effected by having hyssop oil impregnated in the base synthetic resin directly or after dissolving hyssop oil in a suitable solvent such as acetone, or by mixing hyssop oil and a synthetic resin in a molten state. In the latter case, a process may be employed in which the master pellets are first prepared by mixing hyssop oil in a high concentration and a synthetic resin in a molten state, and these master pellets, either directly or after diluted with the base synthetic resin to contain a predetermined amount of hyssop oil, are molded into a desired product such as film, sheet, net, etc., by a method usually used for molding of thermoplastic resins, such as injection molding, inflation, spinning, etc. It is also possible to apply multilayer molding, composite spinning or other molding method according to the purpose of use of the molded product, such as controlling the pest repelling effect retention time.

The content of the active ingredient hyssop oil in said formulations is variable depending on the form of the formulation, method of application and other factors, but in the case of the liquid or cream formulations, the hyssop oil content is usually 0.1 to 50% by weight, preferably 1 to 20% by weight. In the case of resin moldings, the hyssop oil content is usually 1 to 40% by weight, preferably 5 to 30% by weight. When the hyssop oil content in the resin molding is less than 1% by weight, the pest repelling effect of the product is not excellent, and when the hyssop oil content exceeds 40% by weight, hyssop oil may unpreferably bleed out to the molding surface to make it tacky.

In the pest repellent of the present invention, it is possible to blend other types of pest repellent, synergist, antioxidant, UV absorber, insecticide, and other appropriate additives such as dye and pigment.

As other types of pest repellent which can be blended in the formulations of the present invention, there can be exemplified, for example, carane-3,4-diol, DEET, p-menthane-3,8-diol, 2,3,4,5-bis($\Delta^2$-butylene) tetrahydrofurfural, di-n-propylisocine coronate, di-n-butyl succinate, 2-hydroxyoctyl sulfide, and (N-carbo-sec-butyloxy)-2-(2'-hydroxyethyl)-piperidine. As synergist, for instance, N-(2-ethylhexyl)-8,9,10-trinorborne-5-en-2,3-dicarboxyimide (MGK-264) can be used. As antioxidant, for instance, butylhydroxyanisole, dibutylhydroxytoluene, tocopherol, γ-oryzanol and the like can be used. As insecticide, for instance, Empenthrin, Transfluthrin Prallethrin Allethrin, pyrethrin, tetramethrin, phenothrin, Cyphenothrin, permethrin, Cypermethrin, Cyhalothrin, Resmethrin, Cyfluthrin, Fenvalerate, deltamethrin, Tralomethrin, Tefuramethrin, Ethofenprox, Silafluofen, Furamethrin, Imiprothrin, Terallethrin, Metoxadiazone, Propoxur, Fenitrothion, Dichlorovos and the like can be used.

In the present invention, hyssop oil or its formulations may be applied, by suitable means such as sprinkling, spraying, coating or setting, to a pertinent location in the pest accessible area where the repellent effect of hyssop oil or its formulations is desired to be demonstrated (such as walls, floors, furniture, curtains, window screens, etc., of the rooms of a house, kitchen, warehouse, etc.), or to the boundary between said area and the outside or the appropriate locations nearby (such as doors and windows of the rooms of a house, kitchen, warehouse, etc.). It is thereby possible to keep bloodsucking insects as well as other pest such as food pest and harassing pest from entering the house rooms, kitchen, warehouse and other locations where it is desired to repel them. The amount of hyssop oil or its formulations to be applied is variable depending on the place of application, form of the formulation, type of pest to be repelled, etc., but it may for instance be 0.1 to 100 g/m$^2$ calculated as hyssop oil. It is also possible to provide the pest repelling effect by using the plant body (green or dried grass) of hyssop (*Hyssopus officinalis* L.) itself or a pot in which hyssop is planted. That is, pest can be repelled from a location by placing hyssop or its pot there. The amount of Hyssops to be located may be an amount sufficient to repel pest and is variable owing to the degree of their growth. For example, when hyssops grown in about 30 cm of the height are used, they are used in a proportion of 0.05 to 20 plants/m$^3$. Pest repelling effect can also be obtained by wearing a wrist band, cap, clothes, socks or the like treated with hyssop oil or applying hyssop oil or its formulations (aerosol, cream, etc.) directly to the skin.

Hereunder, the present invention will be described in further detail by showing the formulation examples and test examples, but the present invention is not limited to these examples.

First, the formulation examples are shown. In the following descriptions, all "parts" are by weight.

FORMULATION EXAMPLE 1

10 parts of hyssop oil is dissolved in ethanol to make the total amount 35 parts, and the solution is filled in an aerosol container. Then a valve is set to the container and 65 parts of dimethyl ether (propellant) is filled in the container through the valve under pressure to obtain an aerosol.

FORMULATION EXAMPLE 2

10 parts of stearic acid, 2 parts of cetyl alcohol, one part of lanolin, 2 parts of liquid paraffin and 62 parts of water are added to 10 parts of hyssop oil, and melted and mixed under heating, and then 13 parts of heated glycerin is poured into the mixture and stirred well to obtain a cream formulation.

FORMULATION EXAMPLE 3

30 parts of hyssop oil and 70 parts of an ethylene-methyl methacrylate copolymer (Acryft WH202 produced by Sumitomo Chemical Co., Ltd.) are kneaded by a sealed pressure kneader for about 15 minutes and pelletized to prepare master pellets. 100 parts of these master pellets and 200 parts of said ethylene-methyl methacrylate copolymer used as matrix resin are again kneaded by said sealed pressure kneader for 15 minutes, then supplied to an extruder and hot cut while being extruded to obtain pellets having a hyssop oil content of 10% by weight. These pellets are T-die extruded to obtain a sheet of 1 mm thickness.

FORMULATION EXAMPLE 4

A 25% w/v acetone solution of hyssop oil was prepared. One ml of this solution was applied to a 20 cm×2.5 cm filter paper and air dried, and this filter paper was made into a ring shape to obtain a pest-repellent wrist band.

FORMULATION EXAMPLE 5

5 parts of hyssop oil, 2 parts of carane-3,4-diol and 0.2 part of Allethrin are dissolved in isopropanol to make the total amount 25 parts, and the solution is filled in an aerosol container. 30 parts of deionized water is further added. Then a valve is set to the container and 45 parts of dimethyl ether is filled in the container through the valve under pressure to obtain an aerosol.

Next, usefulness of hyssop oil for repelling of pests is demonstrated by the following test examples.

TEST EXAMPLE 1

A lower side part of a plastic cup (base diameter: 10 cm; top opening diameter: 12 cm; height: 7 cm; capacity: about 650 ml) was cut out to form a 2 cm square entrance of mosquitoes. At the center of said cup was placed a twofold disposal warmer (Kiribai New Hand Warmer, 24-hour type, 13.5×10 cm) as a lure for mosquitoes. A 9 cm-diameter filter paper was treated with a 1 ml solution of the test substance diluted with acetone to a predetermined concentration, and after acetone was air dried, said filter paper was attached to the inside of the cover of said cup with a double-side adhesive tape. This cover was fitted on said cup, allowing the test substance to volatilize and diffuse in the cup for one minute.

In a nylon gauze-made cage (50 cm×50 cm×50 cm) holding about 600 mosquitoes (*Aedes aegypti*) one to 2 weeks old after emergence (sex ratio=ca. 1:1), 2 said cups were placed cater-cornered across the cage, each of said cups being positioned about 10 cm away from the cage corner, to lure the mosquitoes. At the remaining cater-cornered positions were placed the two non-treated cups (the cups treated merely with 1 ml of acetone instead of one-ml solution of the test substance diluted with acetone to a predetermined concentration). In order to minimize the influence of the test substance on the non-treated cups, each cup was so positioned that its mosquito entrance would face the cage corner. 10 minutes after setting the cups at said positions in the cage, each cup was taken out of the cage and the number of the female insects attracted into the cup was counted. Based on the obtained result, the insect entrance inhibition rate was calculated from the following equation:

Insect entrance inhibition rate (%)={(number of insects attracted into the non-treated section−number of insects attracted into the treated section)/number of insects attracted into the non-treated section}×100

The test was conducted on a two-replication system. The result is shown in Table 1. The result obtained after conducting the similar test on DEET, a commercially available active ingredient compound for pest repellents, is also shown in Table 1.

TABLE 1

| Test substance | Amount applied (mg/cup) | Entrance inhibition rate (%) |
|---|---|---|
| Hyssop oil | 0.3 | 94 |
| DEET | 0.3 | 38 |

TEST EXAMPLE 2

The same test as in Test Example 1 was conducted on the mosquitoes (*Culex pipiens pallens*) which were 5 to 7 days old after emergence. Since this species of mosquitoes are nocturnal in their habits, luring was continued overnight and observation was made on the morning of the next day. Also, in order to prevent the mosquitoes which have once entered the cups from making a getaway, a tacky trap was attached to the inside surface of each cup. The results are shown in Table 2.

TABLE 2

| Test substance | Amount applied (mg/cup) | Entrance inhibition rate (%) |
|---|---|---|
| Hyssop oil | 3.0 | 90 |
| DEET | 3.0 | −10 |

TEST EXAMPLE 3

The same test as in Test Example 1 was conducted on the houseflies (*Musca domestica*). However, a 1:1 (by weight) mixture of powder milk and sugar was used as a lure in place of a disposal warmer. The results are shown in Table 3.

TABLE 3

| Test substance | Amount applied (mg/cup) | Entrance inhibition rate (%) |
|---|---|---|
| Hyssop oil | 10 | 97 |
| DEET | 100 | 34 |

TEST EXAMPLE 4

The same test as in Test Example 1 was conducted on *Meqaselia spiracularis* by using a maggot rearing medium (a 1:7:14 (by weight) mixture of powdered feed for animals, bran and water) as a lure in place of the disposal warmer. The 50 cm×25 cm×30 cm high cages were used. One cup treated with the test substance and one non-treated cup were set in each cage, and observation was made 30 minutes after setting. The test was conducted on a two-replication system. The results are shown in Table 4.

TABLE 4

| Test substance | Amount applied (mg/cup) | Entrance inhibition rate (%) |
|---|---|---|
| Hyssop oil | 10 | 92 |
| DEET | 100 | 34 |

TEST EXAMPLE 5

The same test as in Test Example 4 was conducted on *Clogmia albipunctata*. However, the cage was placed in the dark, and observation was made 2 hours after setting the cups in the cage. The results are shown in Table 5.

TABLE 5

| Test substance | Amount applied (mg/cup) | Entrance inhibition rate (%) |
|---|---|---|
| Hyssop oil | 30 | 100 |
| DEET | 30 | 50 |

TEST EXAMPLE 6

A lower end of a 4.5 cm×4.5 cm×4.5 cm carton was cut out to form a 0.5 cm×4.5 cm entrance of insects. A filter paper (2 cm×2 cm) impregnated with an acetone-diluted solution of the test substance was placed in the carton, and a 1 cm×1 cm piece of wool muslin was laid on said filter paper. This carton was set at a corner of a nylon gauze-made cage (20 cm×20 cm×30 cm), and a carton containing a filter paper not treated with hyssop oil and having wool muslin laid thereon was set at the diagonally opposite corner of the cage.

About 60 female adults of *Tineola bisselliella* one to 2 days old after emergence were released in the cage, and the number of the insects which entered the cartons was counted. The test was conducted on a two-replication system. The results are shown in Table 6.

TABLE 6

| Test substance | Amount applied (mg/cup) | Entrance inhibition rate (%) |
|---|---|---|
| Hyssop oil | 1 | 50 |
| DEET | 1 | 9.5 |

TEST EXAMPLE 7

The predetermined part of one forearm of the experimentalist was covered with a glove and a supporter so that a 10 cm wide portion above the wrist alone would be exposed. The wrist band made in Formulation Example 4 was put on the wrist side of the exposed portion, and the experimentalist's arm was inserted into a 50 cm×50 cm×50 cm nylon cage in which 10 female adults of *Aedes aegypti* were released. The time which elapsed until the first and second aedes took the blood-sucking action on the experimentalist's exposed skin was counted. The wrist band was fixed to the skin with an adhesive tape so that it would not move. The same test was conducted on the case where a wrist band non-treated with hyssop oil was put. The experiment was carried out on a 3-replication system. The results are shown in Table 7.

TABLE 7

| | Average time (sec) until the aedes took blood-sucking action | |
|---|---|---|
| | 1st aedes | 2nd aedes |
| Formulation Example 4 | >120 | >120 |
| No treatment | 12 | 19 |

[Effect of the Invention]

The present invention provides an effective pest repellent and a pest repelling method.

What is claimed is:

1. A method for repelling mosquitos which comprises applying an amount of hyssop oil effective to repel said mosquitos from a location from where it is desired to repel said mosquitos.

2. A method of repelling mosquitos which comprises applying a mosquito repelling effective amount of hyssop oil to a subject's skin.

3. A method according to claim 1, wherein the location is at least one area selected from the group consisting of walls, floors, furniture, curtains, and window screens of the rooms of a house, a kitchen, and a warehouse, and the boundary between said selected area and the outside.

4. A method for repelling mosquitos, which comprises wearing a wristband, cap, socks, or clothes treated with a mosquito-repelling amount of hyssop oil.

5. A method according to claim 1, wherein the amount of hyssop oil is 0.1 to 100 $g/m^2$.

6. A method according to claim 3, wherein the amount of hyssop oil is 0.1 to 100 $g/m^2$.

* * * * *